United States Patent
Sahin et al.

(10) Patent No.: US 9,943,076 B2
(45) Date of Patent: Apr. 17, 2018

(54) BORON ADDED CELL CRYOPRESERVATION MEDIUM

(71) Applicant: YEDITEPE ÜNIVERSITESI, Istanbul (TR)

(72) Inventors: Fikrettin Sahin, Istanbul (TR); Selami Demirci, Istanbul (TR); Aysegul Dogan, Istanbul (TR)

(73) Assignee: YEDITEPE ÜNIVERSITESI, Istanbul (TR)

( * ) Notice: Subject to any disclaimer, the term of this patent is extended or adjusted under 35 U.S.C. 154(b) by 90 days.

(21) Appl. No.: 14/913,354

(22) PCT Filed: Aug. 13, 2014

(86) PCT No.: PCT/TR2014/000316
§ 371 (c)(1),
(2) Date: Feb. 20, 2016

(87) PCT Pub. No.: WO2015/026307
PCT Pub. Date: Feb. 26, 2015

(65) Prior Publication Data
US 2016/0205922 A1    Jul. 21, 2016

(30) Foreign Application Priority Data
Aug. 20, 2013  (TR) .............................. a 2013 09923

(51) Int. Cl.
*A01N 1/02* (2006.01)

(52) U.S. Cl.
CPC ........... *A01N 1/0221* (2013.01); *A01N 1/021* (2013.01)

(58) Field of Classification Search
CPC .............................. A01N 1/0221; A01N 1/021
See application file for complete search history.

(56) References Cited

U.S. PATENT DOCUMENTS

2011/0081363 A1   4/2011   Whitney et al.
2013/0059381 A1   3/2013   Mo et al.

FOREIGN PATENT DOCUMENTS

EP    0367271 A2    5/1990
EP    0813361 B1    12/1997

OTHER PUBLICATIONS

Taskli Pakize Neslihan et al "Boron Enhances Odontogenic and Osteogenic Differentiation of Human Tooth Germ Stem Cells(hTGSCs) In Vitro", Biological Trace Element Research Humana Press,Clifton,NJ,US, vol. 153, No. 1, Apr. 12, 2013(Apr. 12, 2013),pp. 419-427, Cytotoxicity Assay;p. 419-427, Cytotoxicity Assay p. 420 right-hand column,p. 421 right-hand column, paragraph 1.
Xiaozhou Ying et al:"Effect of Boron on Osteogenic Differentiation of Human Bone Marrow Stromal Cells.", Biological Trace Element Research, Humana Press Inc,New York,vol. 144, No. 1-3, May 31, 2011(May 31, 2011),pp. 306-315.
Miller Danforth P et al"Stabilization of lactate dehydrogenase following freeze-thawing and vacuum-drying in the presence of trehalose and borate",Pharmaceutical Research, Springer New York LLC, US, vol. 15, No. 8, Aug. 1, 1998(Aug. 1, 1998), pp. 1215-1221.
Demirci Selami et al"Boron increases the cell viability of mesenchymal stem cells after long-term cryopreservation", Cryobiology,vol.68,No.1,Jan. 21, 2014(Jan. 21, 2014), pp. 139-146.
Buchanan.S.S.,Gross,S.A.,Acker,J.P.,Toner,M.,Carpenter,J.F.,and Pyatt.D.W.,Cryopreservation of stem cells using trehalose evaluation of the method using a human hematopoietic cell line. Stem cells and development, 13(3), 295-305.
Carpenter, J. F., and Hansen, T. N. (1992).Antifreeze protein modulates cell survival during cryopreservation:mediation through influence on ice crystal growth. Proceedings of the NationalAcademy of Sciences, 89(19), 8953-8957.
Goldbach, H. E., Huang, L., and Wimmer, M. A. (2007)."Boron functions in plants and animals:recent advances in boron research and open questions." InAdvances in Plant and Animal Boron Nutrition (pp. 3-25). Springer Netherlands.
Gonda, K., Shigeura, T., Sato, T., Matsumoto, D., Suga, H., Inoue. K., and Yoshimura K. (2006).Preserved proliferative capacity and multipotency of human adipose-derived stem cells after long-term cryopreservation. Plastic and reconstructive surgery, 121(2), 401-410.
Stachecki, J. J., Cohen, J., and Willadsen, S. (1998).Detrimental effects of sodium during mouse oocyte cryopreservation. Biology of reproduction, 59(2), 395-400.
Woods, E. J., Perry, B. C., Hockema, J. J., Larson, L., Zhou, D., and Goebei, W. S. (2009)."Optimized cryopreservation method for human dental pulp-derived stem cells and their tissues of origin for banking and clinical use." Cryobiology, 59(2), pp. 150-157.

*Primary Examiner* — Kara Johnson
(74) *Attorney, Agent, or Firm* — Gokalp Bayramoglu

(57) ABSTRACT

The present invention relates to a cryopreservation (freezing) medium which can be used for long-term storage of cell lines, tissue samples, sperms, oocytes and embryos. The invention enables to freeze and store cells without affecting cell viability, to increase cell viability and to protect multipotent properties of the cells. The invention facilitates freezing and storing sperms, eggs, embryos, plant cells and materials, cancer and sensitive cell lines, stem cells (embryonic and mesenchymal), blood and blood cells and biological material and organs.

6 Claims, 3 Drawing Sheets

US 9,943,076 B2

BORON ADDED CELL CRYOPRESERVATION MEDIUM

FIELD OF THE INVENTION

The present invention relates to a cryopreservation (freezing) medium which can be used for long-term storage of cell lines, tissue samples, sperms, oocytes and embryos.

BACKGROUND OF THE INVENTION

The cryopreservation (freezing) process is the preserving of a cell, tissue or a full organism at temperatures below zero degrees Celsius under suitable conditions and in the presence of chemicals. It is aimed to stop enzymatic and chemical reactions at lower temperatures and store the materials without getting damaged further. In order to stop all biological activity and realize the most effective biological freezing process, liquid nitrogen (−196° C.) and vapor are preferred. There are cryoprotectants which are developed for this purpose and which protect the material that will be frozen against freeze-thaw stress. The most important detrimental effect of the freezing process is accumulation of the water in the living system in intercellular and intracellular areas which form of ice crystals due to decreasing of the temperature (Carpenter, and Hansen, 1992). The freezing and thawing process is performed by slowly decreasing the temperature which stops biological activities and then rapidly warming and transferring into a normal culture medium. One of the events which occur during this application and which is known to have detrimental effects is the "solution effect" (medium effect). This effect is caused by the metabolites accumulating in the small amount of liquid medium remaining after ice formation. Following the slow freezing process, the cells are exposed to these metabolites for a prolonged period of time (Stachecki et al., 1998). Another detrimental effect is the intracellular liquid flowing out of the cell and forming ice crystals in the intercellular area as a consequence of slow freezing application. Chemicals such as glycerol, dimethyl sulfoxide (Me2SO) and 1,2 propandiol (PrOH) are used during freezing process and they replace water enabling it to flow out of the cell. This is used for eliminating the detrimental effects of the freezing process (Stachecki et al., 1998). As much as the freezing process should be performed slowly, thawing process should be performed rapidly. The rapidly thawed cells should be quickly transferred to a healthy culture medium in order to get rid of the toxic effects of the chemicals used in the freezing process (Buchanan et al., 2004). In this case, freezing media and methods which are non-toxic, can increase cell viability, and can provide effective protection are needed. An effective cell cryopreservation process is needed for embryos, sperm and egg cells and important cell lines such as stem cells. Storage of stem cells and particularly of mesenchymal stem cells, and establishing stem cell banks are necessary for therapeutic applications (Woods et al., 2009). Storage of the stem cells under suitable conditions is extremely important to be able to use them effectively in therapy. Long-term freezing and storage is required for the cells to maintain their multipotent properties, to be stocked at large numbers and to be easily transported (Gonda et al., 2008). Boron is a trace element which is known to be important particularly in plants. In mammalian system, it forms cell membrane glycoproteins and diester borate complexes and functions as a redox regulator and also affects membrane structure and function (Goldbach et al., 2007).

European patent document no. EP0813361B1 relates to a medium used for freezing the cells, particularly the erythroid progenitor cells in blood.

United States patent document no. US20130059381A1 relates to a cell cryopreservation solution that can be used for non-programmed cell cryopreservation.

SUMMARY OF THE INVENTION

An objective of the present invention is to provide a medium which enables the freezing of cells without damaging cell viability.

Another objective of the present invention is to provide a cryopreservation (freezing) medium which decreases the stress that occurs during freezing and reduces dimethyl sulfoxide (Me2SO) concentration.

A further objective of the present invention is to provide a cryopreservation medium which increases cell viability by reducing Me2SO amount.

Another objective of the present invention is to provide a cryopreservation medium which facilitates storage, transportation and stocking of cells.

A further objective of the present invention is to provide a cryopreservation medium which enables long-term freezing and storage of the cells, protection of their multipotent properties and stocking them at large numbers.

Another objective of the present invention is to provide a cryopreservation medium which facilitates freezing and storing sperms, eggs, embryos, plant cells and materials, cancer and sensitive cell lines, stem cells (embryonic and mesenchymal), blood and blood cells, and biological material and organs.

A further objective of the present invention is to provide a cryopreservation medium which prevents intracellular fluid from flowing out of the cell and forming ice crystals at the intercellular area during freezing.

BRIEF DESCRIPTION OF THE DRAWINGS

"Boron Added Cell Cryopreservation Medium" was developed to fulfill the objectives of the present invention and is illustrated in the accompanying figures wherein.

DETAILED DESCRIPTION OF THE INVENTION

Cytotoxicity Analyses

Cell viability analyses were performed with 13 different concentrations ranging between 5 μg/ml and 700μ/ml in order to show whether sodium pentaborate pentahydrate has toxic effect on human tooth germ stem cells. The stock solution was dissolved in sodium pentaborate pentahydrate medium at 10 mg/ml and was made ready by being filtered through a 0.22 μm filter. The intermediate concentrations to be applied on the cells were prepared in the cell culture medium and were applied on the human tooth germ stem cells.

Freezing Procedure

During the freezing process, different from the standard protocol, 20 μg/ml NaB was added to the cell cryopreservation medium. The control group was incubated by a standard cryopreservation medium. During freezing of the cells, different amounts of Me2SO (10%, 7%, 5% and 3% Me2SO) were added to the medium which contained 20% FBS (Fetal Bovine Serum) and 1% PSA (penicillin streptomycin amphotericin) in addition to 20 μg/ml NaB. Except for the group which was frozen for an extended period (6 months), the other cells were subjected to 4 repeating freeze-thaw processes. During each freezing process, one million cells were placed into one freezing tube and were frozen to −80° C. by using a freezing tank. The freezing tubes were transferred to −196° C. liquid nitrogen vapor one day later. After each freezing process, the cells were rapidly molten in a 37° C. water bath and viability analyses were performed with trypan blue.

Differentiation Studies

The cells frozen for an extended period were thawed and subjected to differentiation experiments in order to determine whether 20 μg/ml of NaB, which was used during freezing process—different from the standard procedure—, had any effect on mesenchymal cell differentiation. Osteogenic, chondrogenic and adipogenic differentiation-induced cells were subjected to staining (von Kossa, Alcian Blue and Oil red) and immunocytochemistry (Col I, Col II, Osteocalcine, FABP4) analyses to show that no difference was formed after differentiation.

Statistical Analyses

Statistical analyses were performed by using student-t test and Graph-Pad Prism program.

Experimental Results

Figure 1:
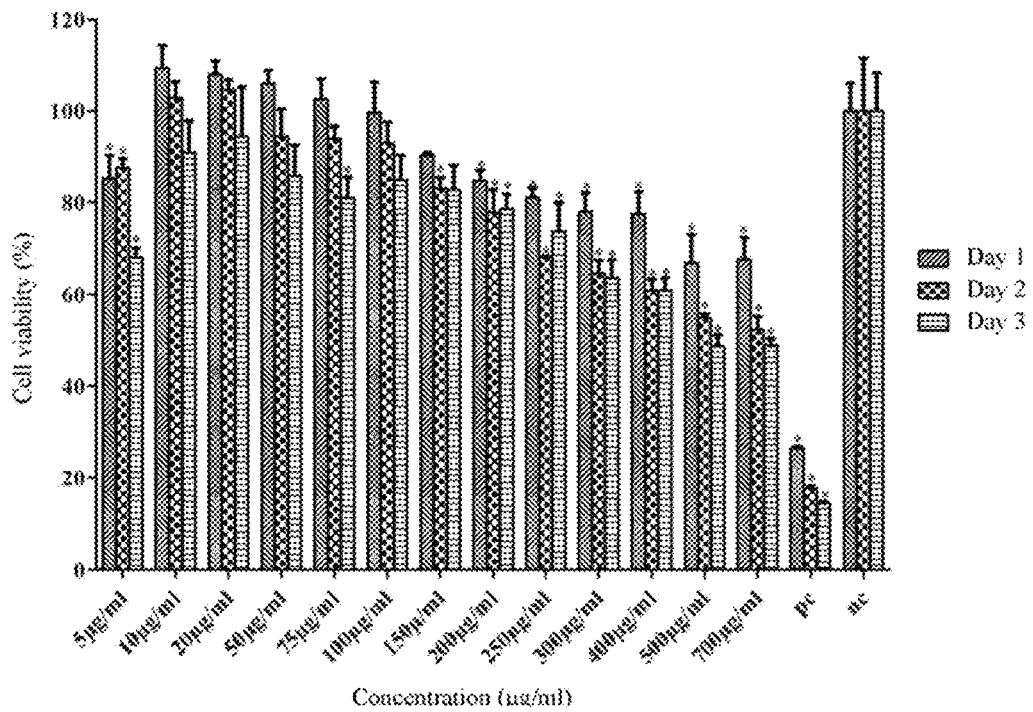
FIG. 1 is the view of the effect of sodium pentaborate pentahydrate (NaB) on cell viability for a period of three days (nc: negative control, pc: positive control $*p<0.05$).
Figure 2:
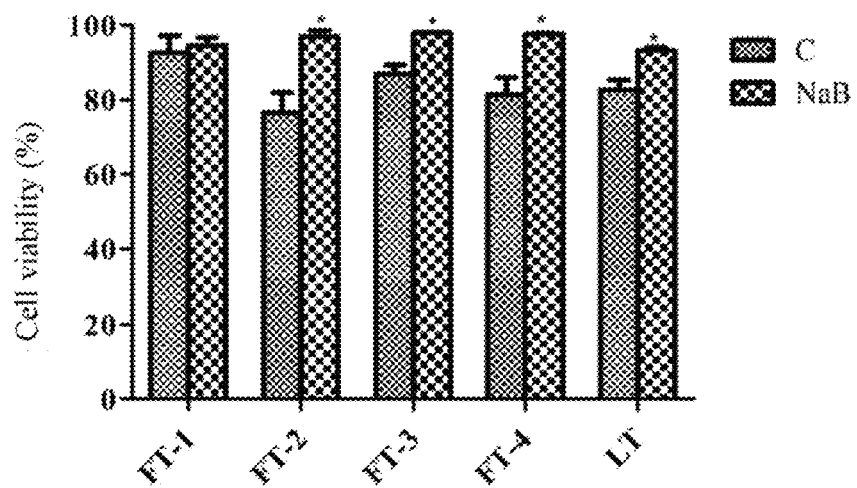
FIG. 2 is the view of the effect of the NaB containing cryopreservation medium on cell viability after repeating and long-term freezing (nc: negative control, NaB: sodium pentaborate pentahydrate, FT: freeze-thaw process $*p<0.05$).
Figure 3:
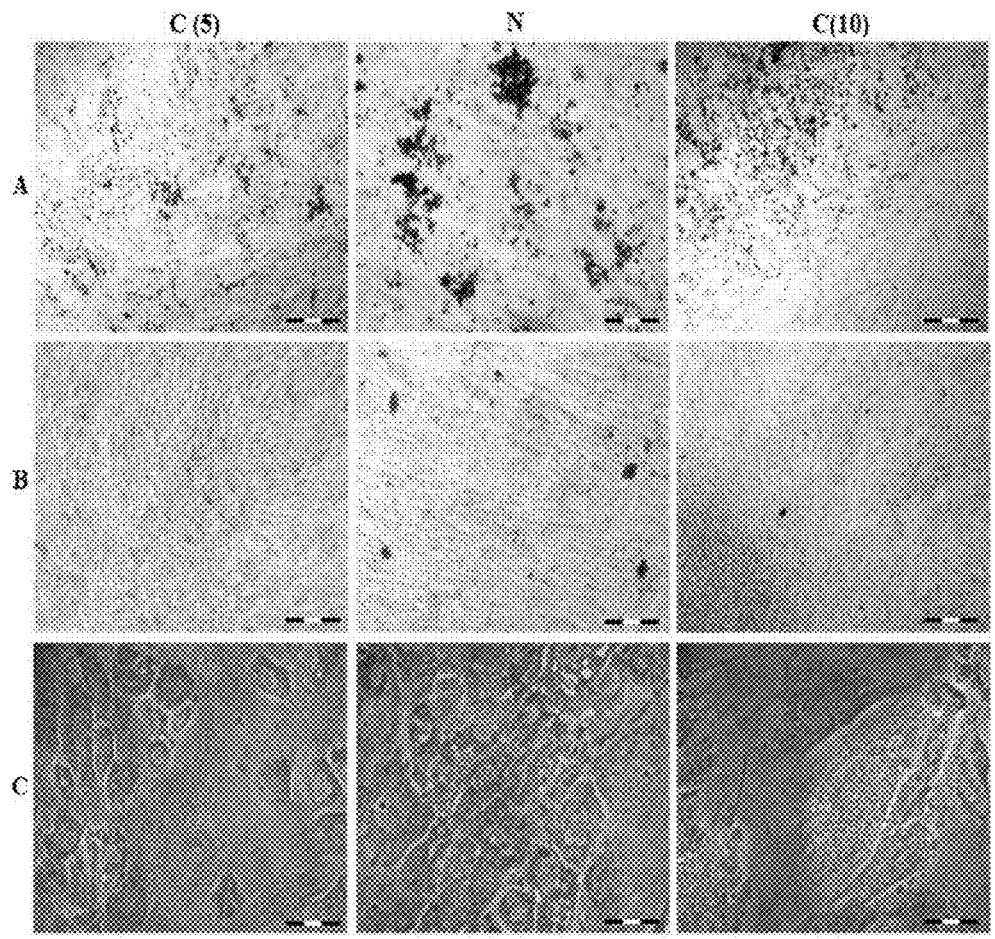
FIG. 3 is the view of the last state of the human tooth germ stem cells after von Kossa (A), Alcian blue (B) and Oil red (C) staining. (von Kossa shows odontogenic differentiation, Alcian blue shows chondrogenic differentiation, and oil red shows adipogenic differentiation). (C(5): Control frozen with 5% Me2SO, N: NaB+5% Me2SO, C(10): Standard control group frozen with 10% Me2SO) (Magnifying scale: 400 μm)
Figure 4:
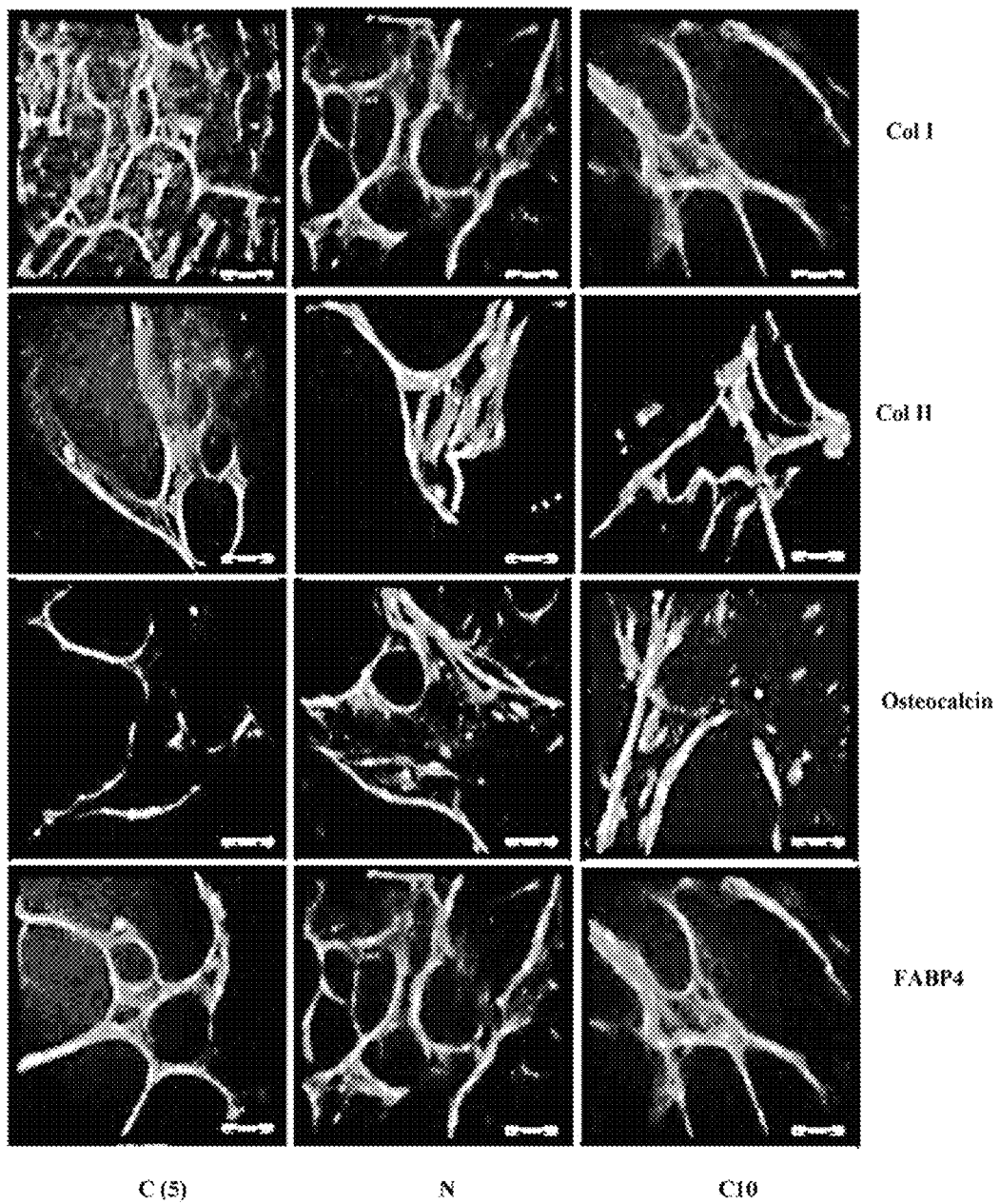
FIG. 4 is the representation of bone, cartilage and adipose differentiation with immunocytochemistry analysis. Col I and Osteocalcine show bone differentiation, Col II shows cartilage differentiation and FABP4 shows adipose differentiation. (C(5): Control frozen with 5% Me2SO, N: NaB+ 5% Me2SO, C(10): Standard control group frozen with 10% Me2SO) (Scale bar: 100 μm)

Cell viabilities were completed to determine the suitable pentaborate pentahydrate concentration to be applied before starting the freezing experiments. Toxic effect was observed in three days at concentrations of 200 μg/ml and above (FIG. 1). Among the concentrations which did not have any negative impact on cell viability, 20 μg/ml of NaB was selected to be used in the freezing experiments. As a result of the cell viability analysis of the cells which were repeatedly frozen and the cells which were frozen and stored for long term, it was observed that use of 20 μg/ml NaB in the presence of 5% Me2SO decreased toxic effect. Thus use of 5% Me2SO in the cryopreservation medium made it possible to increase cell viability. It was observed that cell viability started to increase during and after the second freeze-thaw process (FIG. 2). The cells in the group to which 5% Me2SO was applied were thawed after a long term freezing experiment and differentiation tests were conducted thereon for characterizing their mesenchymal properties. Following the differentiation experiments, while an increase was observed in differentiation of the cells into odontogenic and chondrogenic lineages, a slight decrease was observed in stem cell differentiation into adipose tissue. According to the staining and immunocytochemistry analyses, it was found that there was no significant change in the differentiation potentials of the cells (FIG. 3-4).

Application of the Invention

The invention is a cryoprotectant freezing (cryopreservation) medium which prevents the damage that might occur in the cells and tissues during the freeze-thaw process. The said invention is used for storing living tissues such as pancreatic islets, skin, cornea, cardiac valves, veins, blood and blood cells, umbilical cord blood and tissue, and organ and tissue pieces which are important for transplantation therapy. Additionally, it can also be used for long-term storage of stem cells that can be used in tissue regeneration and gene therapy such as hematopoietic stem cells, mesenchymal stem cells, embryonic stem cells, IPS cells (induced pluripotent stem cells). The invention can be used for storing cancer cells, primary cell lines (fibroblast, keratinocyte, etc.) and immortalized cell lines, used in the experimental studies. The said invention can be used for storage of human and animal sperms, eggs, testicle, and ovarian tissues which can be stored for use in in vitro fertilization purposes.

The invention claimed is:

1. A cryopreservation medium comprising:
   20 μg/ml sodium pentaborate pentahydrate (NaB);
   20% fetal bovine serum (FBS);
   1% of penicillin streptomycin amphotericin (PSA) and
   10%, 7%, 5% or 3% dimethyl sulfoxide (Me2SO).

2. A storage method using a cryopreservation medium, the method comprising the following steps:
   1) adding 10%, 7%, 5% or 3% dimethyl sulfoxide (Me2SO) to a medium comprising 20% fetal bovine serum (FBS), 1% penicillin streptomycin amphotericin (PSA) and 20 μg/ml sodium pentaborate pentahydrate (NaB) to obtain the cryopreservation medium;
   2) placing a sample to be stored into a freezing tube;
   3) freezing the freezing tube to −80° C.; and
   4) further freezing the freezing tube to −196° C.

3. The storage method according to claim 2, wherein the sample in step 2) is selected from a group consisting of pancreatic islets, skin, cornea, cardiac valves, veins, blood and blood cells, umbilical cord blood and tissue, and organ and tissue pieces.

4. The storage method according to claim 2, wherein the sample in step 2) is selected from a group consisting of hematopoietic stem cells, mesenchymal stem cells, embryonic stem cells and induced pluripotent stem cells (IPS cells).

5. The storage method according to claim 2, wherein the sample in step 2) is selected from a group consisting of cancer cells, primary cell lines and immortalized cell lines.

6. The storage method according to claim 2, wherein the sample in step 2) is selected from a group consisting of human and animal sperms, eggs, testicle and ovarian tissues.

* * * * *